United States Patent
Windhab et al.

(10) Patent No.: US 10,406,098 B2
(45) Date of Patent: Sep. 10, 2019

(54) INJECTION SOLUTION COMPRISING A NON-NUCLEOSIDE REVERSE-TRANSCRIPTASE INHIBITOR AND POLY(LACTIDE-CO-GLYCOLIDE)

(71) Applicant: Evonik Roehm GmbH, Darmstadt (DE)

(72) Inventors: Norbert Windhab, Hofheim (DE); Rima Jaber, Frankfurt (DE); Axel Schroeder, Reinheim (DE); Kevin Burton, Hoover, AL (US); Tom Tice, Indian Springs, AL (US)

(73) Assignee: Evonik Roehm GmbH, Darmstadt (DE)

( * ) Notice: Subject to any disclaimer, the term of this patent is extended or adjusted under 35 U.S.C. 154(b) by 0 days.

(21) Appl. No.: 15/776,043

(22) PCT Filed: Nov. 11, 2016

(86) PCT No.: PCT/EP2016/077402
§ 371 (c)(1),
(2) Date: May 14, 2018

(87) PCT Pub. No.: WO2017/084973
PCT Pub. Date: May 26, 2017

(65) Prior Publication Data
US 2018/0318211 A1 Nov. 8, 2018

Related U.S. Application Data

(60) Provisional application No. 62/255,866, filed on Nov. 16, 2015.

(30) Foreign Application Priority Data

Dec. 3, 2015 (EP) .................................. 15197777

(51) Int. Cl.
  *A61K 31/505* (2006.01)
  *A61K 9/00* (2006.01)
  *A61K 47/22* (2006.01)
  *A61K 47/34* (2017.01)
  *A61K 31/536* (2006.01)
  *A61K 45/06* (2006.01)

(52) U.S. Cl.
  CPC .......... *A61K 9/0024* (2013.01); *A61K 31/505* (2013.01); *A61K 31/536* (2013.01); *A61K 45/06* (2013.01); *A61K 47/22* (2013.01); *A61K 47/34* (2013.01)

(58) Field of Classification Search
  CPC .................................................. A61K 31/505
  See application file for complete search history.

(56) References Cited

U.S. PATENT DOCUMENTS

| 5,278,201 | A | 1/1994 | Dunn et al. |
| 6,537,972 | B1 | 3/2003 | Holzmayer et al. |
| 6,565,874 | B1 | 5/2003 | Dunn et al. |
| 8,017,144 | B2 | 9/2011 | Dumont et al. |
| 8,470,359 | B2 * | 6/2013 | Dunn ................... A61K 9/0024 424/426 |
| 2006/0106043 | A1 * | 5/2006 | Kraft ................. A61K 31/4433 514/269 |
| 2016/0008374 | A1 * | 1/2016 | Geleziunas .......... A61K 31/437 424/160.1 |
| 2017/0246118 | A1 * | 8/2017 | Johns ................... A61K 9/0019 |

FOREIGN PATENT DOCUMENTS

| WO | WO99/64048 | * 12/1999 |
| WO | 2009/042194 | 4/2009 |

OTHER PUBLICATIONS

Hare et al. CAS: 157: 780, 2011.*
Barre-Sinoussi et al., "Isolation of a T-lymphotropic retrovirus from a patient at risk for acquired immune deficiency syndrome (AIDS)," Science, 220, 1983, pp. 868-870.
Gallo et al., "Frequent detection and isolation of cytopathic retroviruses (HTLV-III) from patients with AIDS and at risk for AIDS," Science, 224, 1984, pp. 500-503.
Messiaen et al. "Clinical Use of HIV Integrase Inhibitors: A Systematic Review and Meta-Analysis", PLoS ONE 8(1), 2013, vol. 8, Is. 1. pp. 1-16, e52562, doi:10.1371/journal.pone.0052562.
Quinones-Mateo et al., "HIV1 Fitness: Implications for Drug Resistance, Disease Progression, and Global Epidemic Evolution," 2001, pp. 134-170, HIV Sequence Compendium.
International Search Report mailed in PCT/EP2016/077402 dated Jan. 2, 2017
Written Opinion of the International Searching Authority mailed in PCT/EP2016/077402 dated Jan. 2, 2017.

* cited by examiner

*Primary Examiner* — Rei Tsang Shiao
(74) *Attorney, Agent, or Firm* — Grüneberg and Myers PLLC

(57) ABSTRACT

An injection solution can be used in a pharmaceutical dosage formulation. The injection solution includes an organic solvent, a copolymer, which is a poly(lactide-co-glycolide) dissolved in the organic solvent, and a pharmaceutical active ingredient, which is a non-nucleoside inhibitor of the HIV reverse transcriptase or of the HIV integrase, and which contains aromatic and heterocyclic aromatic or aromatic and heterocyclic aromatic and aliphatic heterocyclic groups, where a content of the pharmaceutical active ingredient is from about 8 to about 25% by weight of the copolymer solution.

16 Claims, 3 Drawing Sheets

INJECTION SOLUTION COMPRISING A NON-NUCLEOSIDE REVERSE-TRANSCRIPTASE INHIBITOR AND POLY(LACTIDE-CO-GLYCOLIDE)

This application is a National Stage entry under § 371 of international Application No. PCT/EP2016/077402, filed on Nov. 11, 2016, and claims priority to European Patent Application No. 15197777.4, filed on Dec. 3, 2015 and to U.S. Provisional Application No. 62/255,866, filed Nov. 16, 2015.

TECHNICAL BACKGROUND

This invention relates to a class of target-specific small molecules used as active pharmaceutical ingredients, capable to interact with their respective sub-units to build binding motifs and their specific interaction and dynamic diffusion behavior with polyester excipients of the Poly-Lactide-Glycolytes and their different applied forms, building a specific dosage form during the injection into body-fluids and body-tissues and the specific pharmacokinetic, pharmaceutical production and medical use advantages especially in combination therapies with other oral or injected pharmaceutical actives or functional dosage forms targeting RNA and DNA or physiological RNA- and DNA-Protein complexes occurring in cellular disease processes.

Immunodeficiency syndrome (AIDS) has its cause in the acquired infection by HIV (Barre-Sinoussi et al., 1983, Science 220:868-870; Gallo et al., 1984, Science 224:500-503). Genetic heterogeneity exists within each of the therapeutically recognized HIV subtypes.

The Virus, typically a genetically polymorphic retroviral RNA-encoded subset infects Immune Cells, the incorporation into the cell and the virus copying processes use cellular human as well as HIV-encoded proteins and enzymes. Two classes of enzymes synthesize the DNA (reverse transcriptase, RT) using the virus RNA and Integrase using the DNA copies to be integrated in the human chromosomal DNA.

The WHO promoted standard therapies inhibit these two enzymes with different molecular binding strategies of synthetic small molecule APIs.

Oral small molecule therapies found their optimal application by using simple immediate release formulation of three such APIs eventually boosted by similar liver enzyme to improve First Pass effects of liver metabolizing the drug before reaching the infected cell's disease target. E.g. in single, double and triple-tablet daily dosing protocols well tolerated e.g. Lamivudine+Efavirenz+Tenofovir and Lamivudine+Zidovudine+Abacavir using both nucleoside/nucleotide-type (NRTIs) and non-nucleoside type (NNRTIs) reverse transcriptase inhibitors with oral doses trypically above 100 mg and below 1 g each per dose.

Recently the therapy spectrum was enlarged by the use of RT- and integrase-inhibitors with again small molecule structures however targeting the DNA-complexes in proximity to the substrate-pocket of the enzyme protein. Those inhibitors are so well tolerated and still high potent so that oral dosing is below 100 mg, injected doses far below 100 mg are reported therapeutically active. This class of compounds are effective in man and introduced as injectable and reported to speculative depot formulation tests. The disadvantages of depot formulations today are the sophistication of processes, such as precision molding and (micro-)encapsulation or macroscopic implant medication.

Epidemiological theory demands to individually lower constantly the serum positive patient's body fluid as well as cellular copy numbers to avoid resistance response via natural error-prone selection of Virus mutations. This stabilizes the virus population in the regime of the treatment for both the individual and the population fate of such devastating resistance and a niche adoption of natural human population is at risk. This is why intervention strategies need options of drugs and drug regime compliance and adherence that are beyond practical reach with oral medication today.

It was the aim of this invention to solve the dilemma that regions with highest HIV infection numbers and rates need common denominator drug combination with lowest prize, highest efficiency individually and best viral niche adaption epidemiologically in the sense that an inbound adherence would allow for rate deflation of new infections Male workers, with income, women, pregnant women and child, girls and newborns using WHO accepted therapy standards technically not established today.

Arts et al. explain on the HIV database HIV Databases www.hiv.lanl.gov/ (last modified 2013) with in vivo and in vitro data the differences of RT-resistance using NNRTIs and NRTIs the latter predominantly binding to the substrate pocket would lead to short quasi-type resistance preservation in order to re-establish virus fitness whereas NNRTIs bind to a lipophilic pocket allosterically changing the enzyme activity, mutations which could be tolerated after release from the drug-selection pressure. The usefulness of the drug depot described here relates to this: the virus is cornered in choices dilemmas and well-tolerated drugs such as AZT (Zidovudine) would oscillate in regime whereas a drug component with long pharmacokinetic tailing would keep one exit closed to escape during virus-cyclic mutations. This is one reason why the very discrete mutation pattern with low cross-resistance between the NNRTIs and the NRTIs lead to less fit viruses compared to the pattern collection in the protease enzyme and a superior medication track record of such combinations. These combination therapies are high genetic barrier therapies. Integrase Inhibitors (II), dolutegravir. Linos Vandekerckhove et al. conclude however in PLOS (2013) that in first-line therapy, integrase inhibitors are superior to other standard regimens. Integrase inhibitor use after virological failure is supported as well by their meta-analysis of 48 clinical studies. Careful use is however warranted when replacing a high genetic barrier drug in treatment-experienced patients switching successful treatment. This would translate into a therapy naive patient strategy with one or two NRTI or one NRTI and one NNRTI as per the low cost solution in Lamivudine and AZT and a depot injection as disclosed.

U.S. Pat. No. 5,278,201 (Dunn et al.) describes biodegradable in-situ forming implants and methods of producing the same. A poly(D,L-lactic acid) formed by polycondensation is dissolved in NMP (N-methyl-2-pyrrolidone) at a ratio of 68:32 polymer to solvent. Sanguinarine, a benzophenanthridine alkaloid with antimicrobial activity, was added to the solution at a concentration of 2% by weight. In a drug release-test 60% of the drug was released in the first day.

U.S. Pat. No. 8,470,359B2 (Dunn et al.) describes sustained release polymers. In an example a 75/25 lactide to glycolide copolymer was dissolved in N-methyl-2-pyrrolidone at a ratio of 45/55.

OBJECT AND SOLUTION

It is known to prepare injection solutions based on an organic solvent with poly(lactide-co-glycolide) copolymers and pharmaceutical active ingredients dissolved in there. The injection solutions are meant to be injected subcutaneously in a mammalian respectively in man as depots for the long lasting release of pharmaceutical active ingredients. In the case of pharmaceutical active ingredients which are inhibitors of the HIV reverse transcriptase or the HIV integrase however the disadvantage of the so called "bolus effect" has been found. The "bolus effect" means an unwanted high initial release of the HIV reverse transcriptase or the HIV integrase from the dissolved copolymer/active ingredient-complex in the first hours after deposit under the skin. The high active ingredient initial release has been deemed to cause an undesired increase in the mutation rate of the HIV population within the patient, which may be a reason or contributes to resistance against or low effectiveness of the HIV therapy. It was an object of the present invention to avoid the disadvantages as discussed. An injection solution for HIV reverse transcriptase or the HIV integrase active ingredient should be provided in which the "bolus effect" is reduced or avoided. Surprisingly it has been found that a bolus effect can be reduced or avoided when the loading of pharmaceutical active ingredient is increased in the injection solution. The pharmaceutical active ingredient may be present at a rate from about 8 to about 25% by weight of the copolymer solution. With Rilpiverine at a concentration of 15% a bolus effect could be completely avoided.

The inventors have found that pharmaceutical active ingredients which are inhibitors of the HIV reverse transcriptase or the HIV integrase and which contain aromatic and heterocyclic aromatic or aromatic and heterocyclic aromatic and aliphatic heterocyclic groups match with poly(lactide-co-glycolide) copolymers when applied in a copolymer solution in a certain range from about 8 to about 25% by weight of the copolymer solution. As an injectable depot form the disadvantages of the bolus effect and partially non-cooperative behaviour can be reduced or avoided. The undesired non-cooperative behaviour may result from heterogeneity of the formulation and precipitate formation. This is shown with the inventive examples of Rilipverine against the non inventive Efavirenz (low solubility and missing heterocyclic aromats).

In all of the examples the load increase of the active ingredient reduces the bolus effect. This indicates that a cooperative supramolecular fluid aggregation phase is formed between the active ingredient (Rilpiverine or partially Efavirenz) with the polymer.

Figure 1:
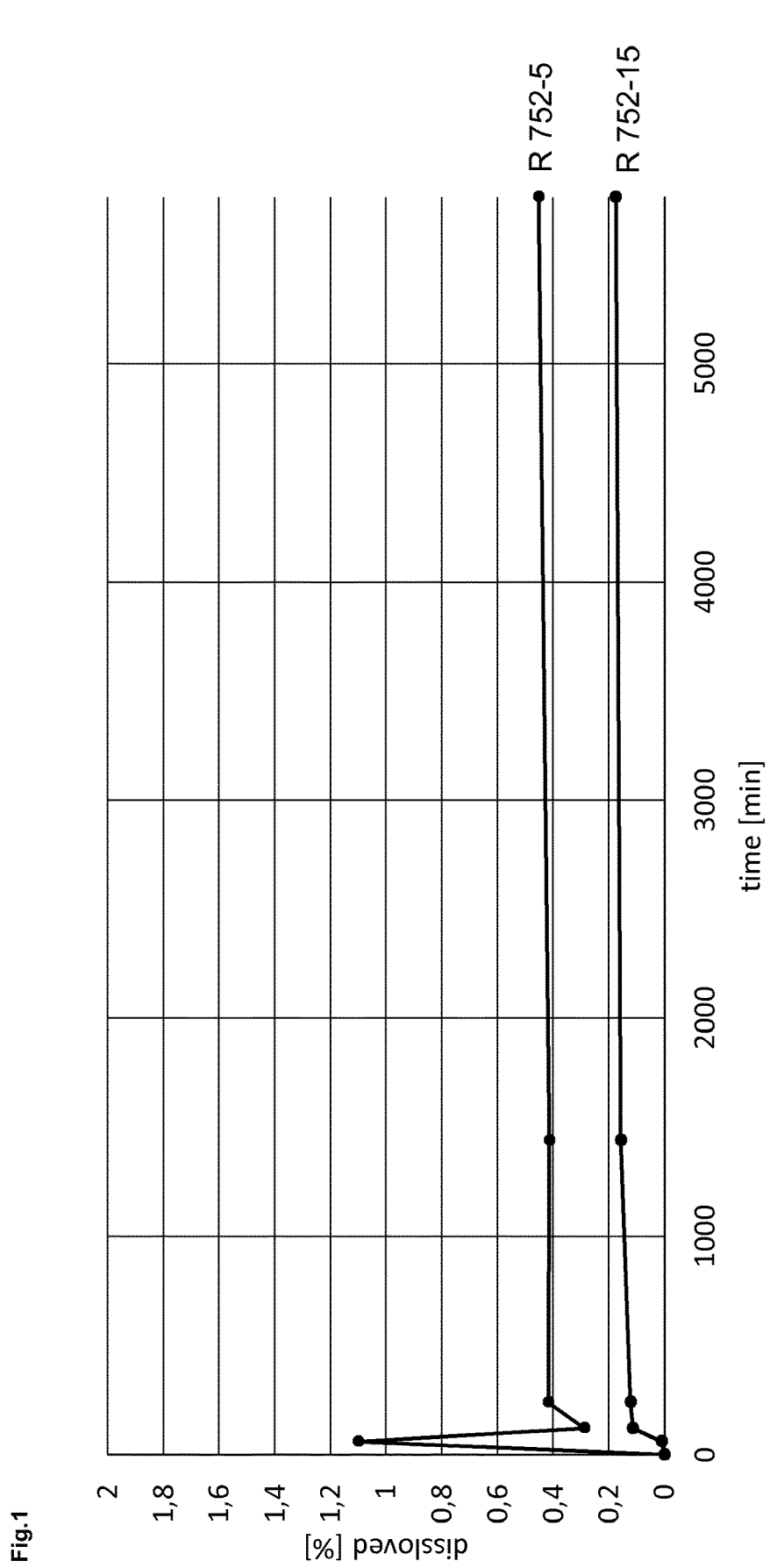
FIG. 1 shows two typical release profiles after water-buffer contact of the Rilipverine formulations R 752-15 (inventive) and R 752-5 (non-inventive). Only R 752-5 shows a bolus effect, while R 752-15 shows no detectable bolus effect.
Figure 2:
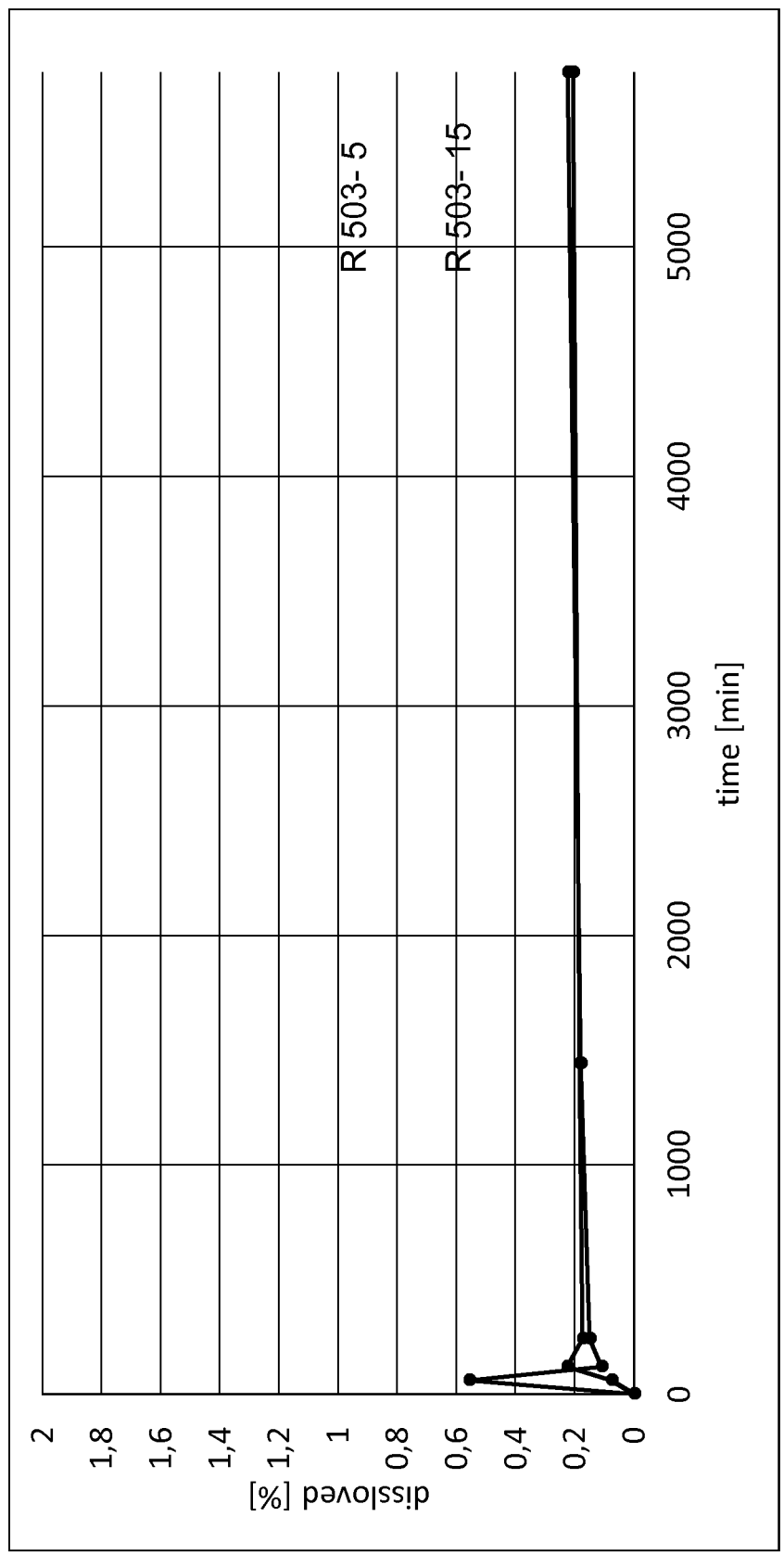
FIG. 2 shows two typical release profiles after water-buffer contact of the Rilpiverine formulations R 503-15 (inventive) and R 503-5 (non-inventive). Only R 503-5 shows a very weak bolus effect, while R 503-15 shows no detectable bolus effect.
Figure 3:
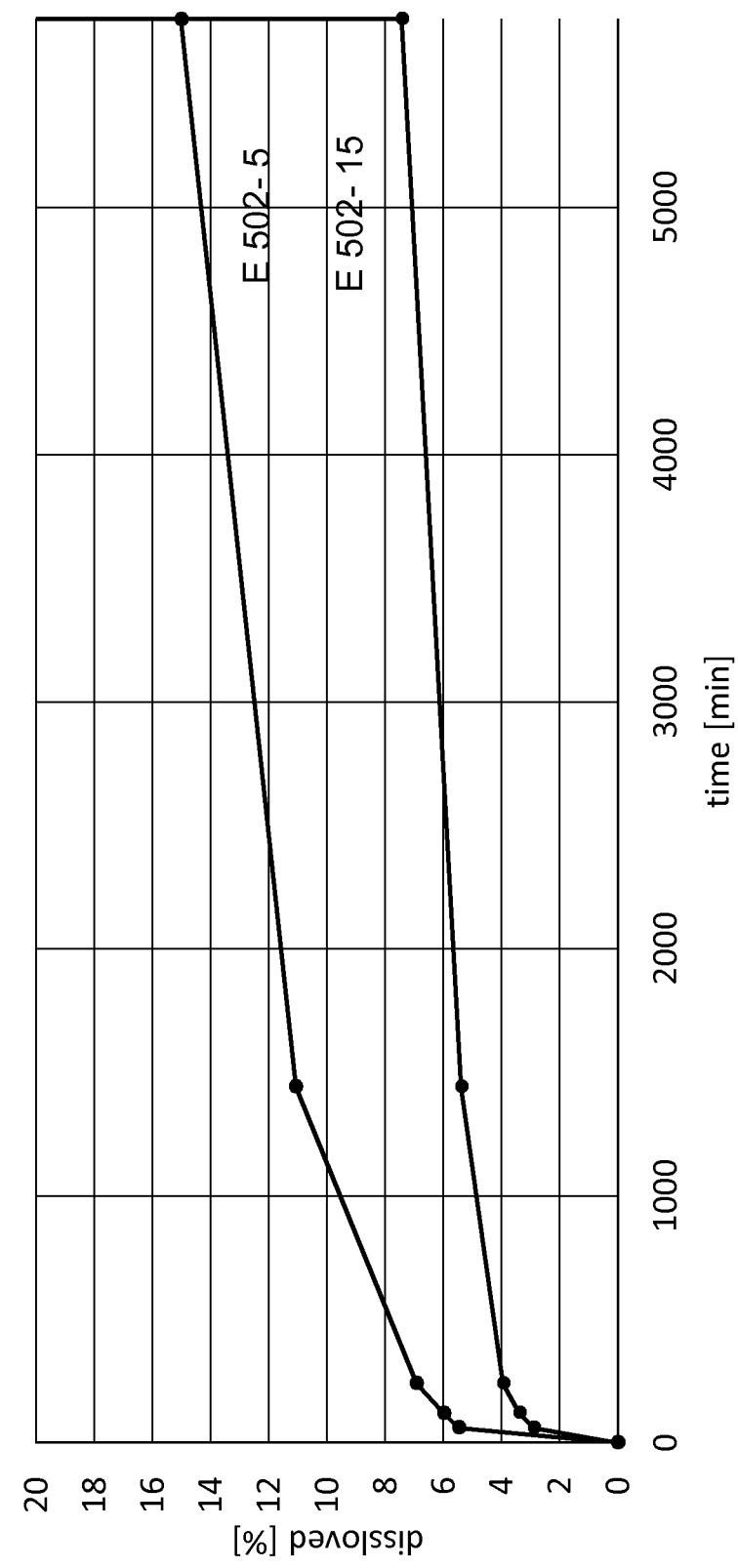
FIG. 3 shows two typical release profiles after water-buffer contact of the non-inventive formulations E 502-15 and E 502-5. The Efavirenz release is so high that it overlays the bolus effect in both curves. It is still distinguishable in E 502-5, E 502-15 does not always show a bolus effect, while the release rate is dramatically slower. It should be noted that the Efavirenz release is much higher than in the examples with Rilpivirine in FIGS. 1 and 2.

The RESOMER® RG 503 (FIG. 2) performs with Rilpiverine in a better way than RESOMER® RG 752 S (FIG. 1), because the bolus effect and the release rate is lower in the case of RESOMER® RG 752 S. Not shown are the result with Rilpiverine and RESOMER® RG 502 (R 502-15 and R 502-5), were bolus and release lies between the curves of FIG. 1 and FIG. 2. Cooperative effect is dependent on the polymer structure. A different API (Efavirenz in FIG. 3) may show biphasic behavior with a free active ingredient present in one phase (fast release) and the cooperative depot in another phase (slow release), resulting in a superposition release of the two phases.

DETAILED DESCRIPTION OF THE INVENTION

The invention is concerned with an injection solution, comprising an organic solvent, a copolymer, which is a poly(lactide-co-glycolide) dissolved in the organic solvent and a pharmaceutical active ingredient which is a non-nucleoside inhibitor of the HIV reverse transcriptase or a non-nucleoside inhibitor of the HIV integrase, which contains aromatic and heterocyclic aromatic or aromatic and heterocyclic aromatic and aliphatic heterocyclic groups, wherein the content of the pharmaceutical active ingredient is from about 8 to about 25%, from about 10 to about 20% or from about 12 to about 18% by weight of the copolymer solution, 8 to 25%, 10 to 20% or 12 to 18% by weight of the copolymer solution, or between 8 and 25%, between 10 and 20% or between 12 and 18% by weight of the copolymer solution.

A preferred ratio of solvent to copolymer may be from 90 to 30 parts of weight solvent to 10 to 70 parts of weight copolymer or from 80 to 40 parts of weight solvent to 20 to 60 parts of weight copolymer. A suitable copolymer concentration in the organic solvent may be from 5 to 50, 10 to 40, 20 to 30, 22 to 28% by weight.

An injection solution is a solution of the copolymer (copolymer solution) and the pharmaceutical active ingredient dissolved or dispersed in the organic solvent respectively in said copolymer solution, which is intended to be injected in a human being as a therapy or part of a therapy against a HIV infection.

Organic Solvent

The injection solution comprises an organic solvent. The organic solvent is preferably capable to diffuse into water, physiological saline, phosphate buffered saline or into mammalian systemic body fluids. This means even if the organic solvent is not completely miscible in water, physiological saline, phosphate buffered saline or into mammalian systemic body fluids, the solvent of said solution will decrease continuously after injection. The organic solvent should be of course biocompatible. This means that with respect to its application undesired side effects or toxic effects are therapeutically acceptable due to its risk/reward evaluation. Physiological saline (about 9 g NaCl in 1 liter water) and phosphate buffered saline may be used in in-vitro systems to simulate the ionic strength of mammalian systemic body fluids.

Suitable organic solvents which are miscible with water, physiological saline, phosphate buffered saline or with mammalian systemic body fluids are N-methyl-2-pyrrolidone, n-methyl-pyrrolidinone, ethanol, propylene glycol, 2-pyrrolidone, acetone, methyl acetate, ethyl acetate, methyl ethyl ketone, dimethylformamide, dimethyl sulfoxide, tetrahydrofuran, caprolactam, decylmethylsulfoxide, a fatty acid, preferably oleic acid or stearic acid, and 1-dodecylazacycloheptan-2-one and any combinations or mixtures thereof.

Copolymer

The copolymer may be dissolved in the organic solvent. A suitable copolymer concentration in the organic solvent may be from 5 to 50, 10 to 40, 20 to 30, 22 to 28% by weight. The copolymer is a poly(lactide-co-glycolide) is preferably a poly(lactide-co-glycolide) with a molar ratio of lactide: glycolide from about 80:20 to about 40:60, most preferably with a molar ratio of lactide:glycolide from about 78:22 to about 45:55.

A poly(lactide-co-glycolide) copolymer (PLGA) is a copolymer that may be polymerized from glycolide and lactide by ring opening polymerization in the presence of a catalyst, such as stannous octanoate.

The copolymers may be produced with acid end groups and with ester end groups. The addition of alkanediols, such as 1,4-butanediol, 2,3-butanediol, 1,6-hexanediol or cyclohexane-1,4-dimethanol, to the reaction mixture leads to copolymers with ester end groups with no titratable carboxylic acid groups in the copolymer. Copolymers with ester end groups are preferred.

A suitable poly(lactide-co-glycolide) copolymer may have a content of polymerized monomer units of 80-40 or 78 t-45 mol % of lactide and 20 to 60 or 22 to 55 mol % of glycolide.

The molecular weight Mw of the PLGA may be in the range of 1.000-50.000, 2.000 to 25.000. The molecular weight Mw of the PLGA may be determined by chromatography in tetrahydrofuran (THF) for instance relative to polystyrene standards or poly(lactic acid)-standards. The glass transition temperature Tg (European Pharmacopeia 7.0 (EP) chapter 2.2.34) of the copolymer may be in the range of 34-48, 35-47° C.

A very suitable copolymer is a poly(D,L-lactide-co-glycolide), 75:25 mol ratio of lactide/glycolide, with an inherent viscosity IV in the range of 0.1-0.3, preferably 0.16-0.24 [IV dl/g]. The glass transition temperature Tg may be in the range of 34-39, 35-38° C. Preferably the end group is an ester end group. (RESOMER® RG 752S).

A very suitable copolymer is a poly(D,L-lactide-co-glycolide), 50:50 mol ratio of lactide/glycolide, with an inherent viscosity IV in the range of 0.1-0.3, preferably 0.16-0.24 [IV dl/g]. ]. The glass transition temperature Tg may be in the range of 39-44, 41-43° C. Preferably the end group is an ester end group. (RESOMER® RG 502).

A very suitable copolymer is a poly(D,L-lactide-co-glycolide), 50:50 mol ratio of lactide/glycolide, with an inherent viscosity IV in the range of 0.26-0.5, preferably 0.32-0.44 [IV dl/g]. ]. The glass transition temperature Tg may be in the range of 43-48, 45-47° C. Preferably the end group is an ester end group. (RESOMER® RG 503).

Inherent viscosity IV: The Inherent viscosity (IV) is preferably determined in an Ubbelohde viscometer of type 0c at 25+0.1° C. utilizing a sample concentration of 0.1% dissolved in chloroform.

Glass Transition Temperatures:

The Glass transition temperature Tg is preferably determined according to the United States Pharmacopeia 36 (USP) chapter <891>, European Pharmacopeia 7.0 (EP) chapter 2.2.34 and according to DIN 53765:1994-03 (D).

The Pharmaceutical Active Ingredient

The pharmaceutical active ingredient (or active pharmaceutical ingredient (API)) may be a non-nucleoside inhibitor of the HIV reverse transcriptase (NNRTI) or of the HIV integrase, which preferably contains aromatic and heterocyclic aromatic or aromatic and heterocyclic aromatic and aliphatic heterocyclic groups at the same time. APIs with an anti-virally active dose of 1 to 150 or below 150, below 100, below 50 mg per day are preferred. The anti-virally active dose means a dose that influences the genetical quasi species of the virus in a specific host.

Preferably the pharmaceutical active ingredient is selected from the group of Etravirine, Rilpivirine and Doravirine.

NNRTIs which contain aromatic and heterocyclic aromatic groups are for instance Etravirine, Rilpivirine and Doravirine.

NNRTIs which contain aromatic and heterocyclic aromatic and aliphatic heterocyclic groups at the same time is for instance Doravirine The NNRTI may be optionally combined with a booster which may be Ritonavir.

A non-nucleoside inhibitor of the HIV integrase is for instance Dolutegravir. Dolutegravir contains aromatic and heterocyclic aromatic and aliphatic heterocyclic groups at the same time.

Injection Solution

The invention is also discloses a process for preparing the injection solution as disclosed by combining the organic solvent in sterile form, the pharmaceutical active ingredient in sterile form and the copolymer in sterile form in a sterile injection device.

The invention also discloses a kit of parts comprising the organic solvent, the pharmaceutical active and the copolymer as disclosed in sterile form, where the pharmaceutical active ingredient and the copolymer are present in dry form in a sterile injection device and the organic solvent is kept separately and can be added into the injection device subsequently.

Methods for sterilization are known to a skilled person and comprise chemical and physical methods. Chemical methods are for instance to contact with ethylene oxide. Physical methods may comprise radiation, preferably gamma-radiation, e-beam gamma radiation.

An injection solution as disclosed, wherein the pharmaceutical active ingredient is Rilpiverine, shows after contact with water an Rilpiverine substraction IR spectrum that shows a shift of the 1568 $cm^{-1}$ vibration band of pure Rilpiverine to a vibration band or supermolecular aggregation band between 1572 and 1576 $cm^{-1}$ or a vanishing 1593 $cm^{-1}$ vibration band of pure Rilpiverine.

A shift shall mean that the 1568 $cm^{-1}$ vibration band of pure Rilpiverine diminishes, while a band, a vibration band or supposed supermolecular aggregation band, between 1572 and 1576 $cm^{-1}$ increases. The 1593 $cm^{-1}$ vibration band of pure Rilpiverine may vanish more or less.

Dispersion

The invention also discloses an injection dispersion comprising the injection solution as disclosed as continuous phase and a further pharmaceutical active ingredient, which is dispersed therein. The further pharmaceutical active ingredient is preferably not soluble in the injection solution as disclosed and thus dispersed in there. The further pharmaceutical active ingredient is preferably a further non-nucleoside reverse transcriptase inhibitor, a nucleoside reverse transcriptase inhibitor or an integrase inhibitor, which is not soluble in the injection solution as disclosed and thus dispersed therein.

The further non-nucleoside reverse transcriptase inhibitor is different from the non-nucleoside reverse transcriptase inhibitor dissolved in the injection solution.

Use

The injection solution as disclosed may be used directly as a pharmaceutical dosage form, which may be used for the HIV treatment of a patient.

The injection solution as disclosed may be used for preparing a pharmaceutical dosage form, which may be used for the HIV treatment of a patient.

The injection solution as disclosed is for use as a pharmaceutical dosage form or for use in preparing a pharmaceutical dosage for the treatment of HIV.

Pharmaceutical Dosage Form

The invention discloses a pharmaceutical dosage form, comprising the injection solution. The pharmaceutical dosage may be present as a kit of parts, which preferably comprises the injection solution, at least one nucleoside reverse transcriptase inhibitor (NRTI), at least one non-nucleoside reverse transcriptase inhibitor (NNRTI) and optionally with a booster, which is a liver enzyme inhibitor. The kit of parts may also comprise a syringe for the application of the injection solution.

The Pharmaceutical dosage form may comprise the injection solution as disclosed or the injection dispersion as disclosed.

Method of Use

The invention is also discloses a method of use of an injection solution in a triple therapy for antiretroviral HIV treatment of a patient, comprising injection of the injection solution as disclosed combined with daily oral fixed dose formulations of at least one nucleoside reverse transcriptase inhibitor (NRTI) and at least one further non-nucleoside reverse transcriptase inhibitor (NNRTI) or the HIV integrase and optionally with a booster, which may be a liver enzyme inhibitor, such as Ritonavir.

A booster may be defined as an inhibitor or a substrate of body enzymes, which shorten the halflife time of a drug. Boosters may be selected from pharmaceutical active ingredients or nutritional ingredients. A suitable bosster may be Ritonavir. The liver enzyme inhibitor may be a proteinase inhibitor which blocks liver enzymes or are substrates of liver enzymes, such as CYP3A, that may break down certain antiretrovirals such as Ritonavir. Thus the boosters such as Cobicistat are intended to improve the so called First Pass effect.

The further non-nucleoside reverse transcriptase inhibitor (NNRTI) may be selected from the group of Efavirenz, Nevirapine or Delavirdine. The further NNRTI is different from the NNRTI which may be already disclosed in the injection solution.

The nucleoside reverse transcriptase (NRTI) inhibitor may be selected from the group of Abacavir, Emtricitabine, Didanosine, Zidovudine, Apricitabine, Stampidine, Elvucitabine, Racivir, Amdoxovir, Stavudine, Tenofovir, Zalcitabine or Festinavir.

Very suitable pairs of nucleoside reverse transcriptase inhibitors (NRTI) or non-nucleoside reverse transcriptase inhibitors (NNRTI) or both that may be added with daily oral fixed dose formulations in the therapy with the injection solution as disclosed may be chosen as follows: Lamivudine and Zidovudine, Lamivudine and Tenofovir, preferably Lamivudine and Efavirenz.

Pairs of nucleoside reverse transcriptase inhibitors (NRTI) and non-nucleoside reverse transcriptase inhibitors (NNRTI) may be used, In the method of use for a the triple therapy for antiretroviral HIV treatment of a patient the following pairs of nucleoside reverse transcriptase inhibitors and non-nucleoside reverse transcriptase inhibitors may be used in combination with a further substances which is a nucleoside reverse transcriptase inhibitor (NRTI) and non-nucleoside reverse transcriptase inhibitors (NNRTI): Lamivudine and Zidovudine, Lamivudine and Tenofovir, Lamivudine and Efavirenz. The pairs are then combined with a further third substance which is a nucleoside reverse transcriptase inhibitors and non-nucleoside reverse transcriptase inhibitors

EXAMPLES

Copolymers Used:

RESOMER® RG 752S: poly(D,L-lactide-co-glycolide), 75:25 mol ratio of lactide/glycolide, with an inherent viscosity IV in the range of 0.16-0.24 [IV dl/g]. The glass transition temperature Tg is about 36.5° C. The copolymer has an ester end group.

RESOMER® RG 502: poly(D,L-lactide-co-glycolide), 50:50 mol ratio of lactide/glycolide, with an inherent viscosity IV in the range of 0.16-0.24 [IV dl/g]. ]. The glass transition temperature Tg is about 41.4° C. The copolymer has an ester end group.

RESOMER® RG 503: poly(D,L-lactide-co-glycolide), 50:50 mol ratio of lactide/glycolide, with an inherent viscosity IV in the range of 0.32-0.44 [IV dl/g]. ]. The glass transition temperature Tg is about 46.5° C. The copolymer has an ester end group.

Example Performance in a standard body-fluid single compartment release experiment Efavirenz In-situ Formulations:

A stock polymer solution was made, using a 5 g of polymer, added to 15 g of n-methyl-pyrrolidinone, the mixture was mixed using the Vortex for 20-30 mins until the polymer was dissolved. Table 1.

Separating the stock solution into about 6,6 g aliquots in 3 different containers.

Adding the Efavirenz into the solution, and mixing it again using the vortex for 20-30 mins, until the API is completely dissolved. Table 2

TABLE 1

| Polymer stock solution | | | |
|---|---|---|---|
| Stock Solution | Polymer | Polymer Weight | n-methyl-pyrrolidinone weight |
| S 752a | RG 752S | 5.089 g | 15.410 g |
| S 502a | RG 502 | 5.048 | 15.027 g |

TABLE 2

| Efavirenz formulations | | | |
|---|---|---|---|
| Formulation Nr. | Polymer | API loading Theoretical | API loading Actual |
| E 752-5 | RG 752S | 5% (wt/wt), | 0.28 g |
| E 752-10 | RG 752S | 10% (wt/wt) | 0.510 g |
| E 752-15 | RG 752S | 15% (wt/wt) | 0.760 g |
| E 502-5 | RG 502 | 5% (wt/wt) | 0.28 g |
| E 502-15 | RG 502 | 15% (wt/wt) | 0.77 g |

Rilpivirine In-Situ Formulations:

A stock polymer solution was made, using a 2,5 g of polymer, added to 7.5 g of n-methyl-pyrrolidinone, the mixture was shacked using the Vortex for 20-30 mins until the polymer was dissolved.

Separating the stock solution into about 5 g aliquots in 2 different containers. Adding the Rilpivirine into the solution, and mixing it again using the vortex for 20-30 mins, until the API is completely dissolved.

TABLE 3

| Polymer stock solution | | | |
|---|---|---|---|
| Stock Solution | Polymer | Polymer Weight | n-methyl-pyrrolidinone weight |
| S 502b | RG 502 | 2.50 g | 7.60 g |
| S 752b | RG 752S | 2.51 g | 7.63 g |
| S 503b | RG 503 | 2.50 g | 7.72 g |

TABLE 4

| Formulations of Rilpivirine | | | |
|---|---|---|---|
| Formulation Nr. | Polymer | API loading Theoretical | API loading Actual |
| R 502-15 | RG 502 | 15% (wt/wt), | 0.8003 g |
| R 502-5 | RG 502 | 5% (wt/wt) | 0.2514 g |
| R 752-15 | RG 752S | 15% (wt/wt) | 0.7930 g |
| R 752-5 | RG 752S | 5% (wt/wt) | 0.26530 g |
| R 503-15 | RG 503 | 15% (wt/wt) | 0.7548 g |
| R 503-5 | RG 503 | 5% (wt/wt) | 0.2530 g |

Release Test:

100 ml of phosphate buffer saline pH 7.4 (PBS, British Pharmacopoeia) are given to a 200 ml volumetric flask. Liquid formulations E and R according to Table 2 and 4 (accounting for (approx.) 10 mg API) were added and immediately showed precipitation or aggregation in the PBS-buffer. PBS-buffer is filled up to 200 ml.

API release studies were performed in triplicate. Samples (2 ml) for HPLC analysis were taken at 0, 1, 2, 4, 24 and 96 hours and centrifuged for 5 minutes at 13400 rpm the supernatant was injected according to the HPLC method in Table 5. At 2, 4 and 24 hours 100 ml of the dissolution medium were pulled and 100 ml of fresh buffer was added (PBS 7.4).

TABLE 5

| HPLC analysis were performed on Agilent 1100 series equipment. | | |
|---|---|---|
| HPLC methods | Efavirenz | Rilpivirine |
| Column | Symetrie 300 C18, 5 μm, 250 mm * 4.6 mm | XTerra C18, 5 μm 150 mm*4.6 mm |
| Mobile Phase | Isocratic: Acetonitrile/ Phosphate buffer pH 3.6 (58/42) (V %/V %) | Isocratic: Methanol LiChrosolv/ Phosphate buffer pH 3.0 (50/50) (V %/V %) |
| Flow rate [ml/min] | 1.5 | 2.0 |
| Injection volume [μl] | 20 | 10 |
| UV wavelength [nm] | 247 | 285 |
| Column temperature [° C.] | ambient | 40 |
| Run time [min] | 10 | 7.5 |
| Retention time [min] | 5.5 | 5.4 |

The Results of the release tests are shown in FIG. 1-3

FIG. 1 shows two typical release profiles after water-buffer contact of the inventive formulation R 752-15 and the non-inventive formulation R 752-5. Only R 752-5 shows a bolus effect, while R 752-15 shows no detectable bolus effect.

FIG. 2 shows shows two typical release profiles after water-buffer contact of the inventive formulation R 503-15 and the non-inventive formulation R 503-5. Only R 503-5 shows a very weak bolus effect, while R 503-15 shows no detectable bolus effect.

FIG. 3 shows shows two typical release profiles after water-buffer contact of the non-inventive formulations E 502-15 and E 502-5. The Efavirenz release is so high that it overlays the bolus effect in both curves. It is still distinguishable in E 502-5, E 502-15 does not always show a bolus effect, while the release rate is dramatically slower. It should be noted that the Efavirenz release is much higher than in the examples with Rilpivirine in FIGS. 1 and 2.

In all of the examples the load increase of the active ingredient reduces the bolus effect. This indicates that a cooperative supramolecular fluid aggregation phase is formed between the active ingredient (Rilpiverine or Efavirenz) with the polymer.

The RESOMER® RG 503 (FIG. 2) performs with Rilpiverine in a better way than RESOMER® RG 752 S (FIG. 1), because the bolus effect and the release rate is lower in the case of RESOMER® RG 752 S. Not shown are the results with Rilpiverine and RESOMER® RG 502 (R 502-15 and R 502-5), were bolus and release lies between the curves of FIG. 1 and FIG. 2. Cooperative effect is dependent on the polymer structure. A different API (Efavirenz in FIG. 3) may show biphasic behavior with a free active ingredient present in one phase (fast release) and the cooperative depot in another phase (slow release), resulting in a superposition release of the two phases.

Spectroscopic Infrared Analysis Characterizing a New Depot Phase Between Copolymer RESOMER® RG 503 and Rilpivirine A Brucker alpha IR-Spectrometer was used to collect spectra of solution and mildly at ambient temperature vacuum-dried Rilpivirine 503 formulation directly to its diamond ATR-surface. As a reference a similar sample "placebo" solution was treated the same way containing only the RESOMER® RG 503 copolymer and no Rilpivirine.

Result:

The N-Methyl-Pyrrolidinon shows a symmetric dominant Peak at 1500 cm-1 and a sharp amid-type vibration peak at 1677 cm-1 proving uncritical for subtraction from the three characteristic double-bond/ring vibrational bands from Rilpivirine [1568cm-1 (strong), 1593 cm-1 and 1614,5 cm-1 (both medium)]. The other dominant polyester band from the PLGA Polymer 1752 cm-1 lies also far from the characteristic triplet of Rilpirivine.

Due to aggregate formation the 1568 cm-1 p shifts perfectly to the baseline oft the solvent substracted spektrum to 1575 cm-1 as the middle peak (1593 cm-1) vanishes nearly completely or could be identified as a shoulder near 1600 cm-1 of the 1614.5 band which stays unchanged as a good internal reference.

The 1575 cm-1 band or the middle band suppression (shift) are characteristic and a supramolecular contact evidence for the novel cooperative Rilpivirine/PLGA (RESOMER® RG 503) supermolecule. Similar to the vibration spectra effect of e.g. Nucleobase Carbonyl- and Ringvibrational shifts in the same spectral region in cooperative double or triple helix DNA/RNA aggregation.

Mildly removing the excess solvent did not alter the band shift effect.

The invention claimed is:

1. An injection solution, comprising:
   an organic solvent,
   a copolymer, which is a poly(lactide-co-glycolide) dissolved in the organic solvent, and
   a pharmaceutical active ingredient, which is at least one member selected from the group consisting of Etravirine, Rilpivirine, Doravirine and Dolutegravir,
   wherein a content of the pharmaceutical active ingredient is from about 8 to about 25% by weight of the copolymer solution.

2. The injection solution according to claim 1, wherein the organic solvent is at least one member selected from the group consisting of N-methyl-2-pyrrolidone, ethanol, propylene glycol, 2-pyrrolidone, acetone, methyl acetate, ethyl acetate, methyl ethyl ketone, dimethylformamide, dimethyl sulfoxide, tetrahydrofuran, caprolactam, decylmethylsulfoxide, a fatty acid, and 1-dodecylazacycloheptan-2-one.

3. The injection solution according to claim 1, wherein the copolymer is a poly(lactide-co-glycolide) with a molar ratio of lactide:glycolide from about 80:20 to about 40:60.

4. The injection solution according to claim 1, wherein the pharmaceutical active ingredient is at least one member selected from the group consisting of Etravirine, Rilpivirine, and Doravirine.

5. The injection solution according to claim 1, where the pharmaceutical active ingredient is Rilpiverine and after contact with water the IR spectrum shows a shift of the 1568 $cm^{-1}$ vibration band of pure Rilpiverine to a vibration band between 1572 and 1576 $cm^{-1}$ or the 1593 $cm^{-1}$ vibration band vanishes.

6. An injection dispersion, comprising:
   the injection solution according to claim 1 as continuous phase, and
   a further pharmaceutical active ingredient which is dispersed therein.

7. The injection dispersion according to claim 6, wherein the further pharmaceutical active ingredient is at least one member selected from the group consisting of a further non-nucleoside reverse transcriptase inhibitor, a nucleoside reverse transcriptase inhibitor, and an integrase inhibitor.

8. A process for preparing the injection solution according to claim 1, the process comprising:
   combining the organic solvent in sterile form, the pharmaceutical active ingredient in sterile form and the copolymer in sterile form in a sterile injection device.

9. A kit, comprising:
   an organic solvent,
   a pharmaceutical active ingredient, and
   the copolymer according to claim 1 in sterile form,
   wherein the pharmaceutical active ingredient and the copolymer are present in dry form in a sterile injection device and the organic solvent is kept separately and can be added into the injection device subsequently.

10. A pharmaceutical dosage form, comprising:
    the injection solution according to claim 1.

11. A kit, which comprises:
    the pharmaceutical dosage form according to claim 10, at least one nucleoside reverse transcriptase inhibitor (NRTI),
    at least one non-nucleoside reverse transcriptase inhibitor (NNRTI), and
    optionally a booster, which is a liver enzyme inhibitor.

12. A triple therapy method of treating a subject with an antiretroviral HIV treatment, the method comprising:
    injecting the injection solution according to claim 1, combined with daily oral fixed dose formulations of at least one nucleoside reverse transcriptase inhibitor or at least one further non-nucleoside reverse transcriptase inhibitor or both and optionally with a booster, which is a liver enzyme inhibitor, into a subject in need thereof.

13. The method according to claim 12, wherein the non-nucleoside reverse transcriptase inhibitor is present and is at least one member selected from the group consisting of Efavirenz, Nevirapine, and Delavirdine.

14. The method according to claim 12, wherein the nucleoside reverse transcriptase inhibitor is present and at least one member selected from the group consisting of Abacavir, Emtricitabine, Didanosine, Zidovudine, Apricitabine, Stampidine, Elvucitabine, Racivir, Amdoxovir, Stavudine, Tenofovir, Zalcitabine, and Festinavir.

15. The method according to claim 12, wherein, in the method the following pairs of nucleoside reverse transcriptase inhibitors and/or non-nucleoside reverse transcriptase inhibitors are included: Lamivudine and Zidovudine, Lamivudine and Tenofovir, and Lamivudine and Efavirenz.

16. A pharmaceutical dosage form, comprising:
    the injection dispersion according to claim 6.

* * * * *